(12) United States Patent
Han et al.

(10) Patent No.: US 9,283,300 B2
(45) Date of Patent: Mar. 15, 2016

(54) USE OF MIDKINE PROTEIN AND THE PROTEIN-CONTAINING MEDICAL DEVICE

(75) Inventors: Wei Han, Shanghai (CN); Zhonghui Zhang, Shanghai (CN)

(73) Assignee: GENERAL REGENERATIVES, LTD, Hong Kong (CN)

( * ) Notice: Subject to any disclaimer, the term of this patent is extended or adjusted under 35 U.S.C. 154(b) by 74 days.

(21) Appl. No.: 13/322,443

(22) PCT Filed: May 25, 2010

(86) PCT No.: PCT/CN2010/000740
§ 371 (c)(1),
(2), (4) Date: Nov. 23, 2011

(87) PCT Pub. No.: WO2010/135915
PCT Pub. Date: Dec. 1, 2010

(65) Prior Publication Data
US 2012/0108516 A1    May 3, 2012

(30) Foreign Application Priority Data
May 27, 2009  (CN) .......................... 2009 1 0052136

(51) Int. Cl.
| | | |
|---|---|---|
| *A61K 38/17* | (2006.01) | |
| *A61P 19/02* | (2006.01) | |
| *A61L 27/54* | (2006.01) | |
| *A61L 27/24* | (2006.01) | |
| *A61L 27/22* | (2006.01) | |
| *A61K 38/18* | (2006.01) | |
| *A61F 2/30* | (2006.01) | |

(52) U.S. Cl.
CPC .............. *A61L 27/227* (2013.01); *A61K 38/18* (2013.01); *A61L 27/54* (2013.01); *A61F 2/30756* (2013.01); *A61F 2002/30677* (2013.01); *A61L 2300/252* (2013.01); *A61L 2300/414* (2013.01); *A61L 2430/06* (2013.01)

(58) Field of Classification Search
None
See application file for complete search history.

(56) References Cited

U.S. PATENT DOCUMENTS

| | | | | |
|---|---|---|---|---|
| 2003/0185794 | A1* | 10/2003 | Colley | 424/85.1 |
| 2004/0176287 | A1* | 9/2004 | Harrison et al. | 514/12 |
| 2004/0265282 | A1* | 12/2004 | Wright et al. | 424/93.21 |
| 2011/0129544 | A1 | 6/2011 | Miyazaki et al. | |

FOREIGN PATENT DOCUMENTS

| | | |
|---|---|---|
| CN | 101601858 | 12/2009 |
| JP | 10-029950 | 2/1998 |
| WO | WO-02/098475 | 12/2002 |
| WO | WO-2008/102568 | 8/2008 |
| WO | WO-2009/152487 | 12/2009 |

OTHER PUBLICATIONS

Akhter et al., J. Biochem., 1998, vol. 123:1127-1136.*
Katz, J.N., Best Practice & Research Clinical Rheumatology, 2006, vol. 20(1): 145-153.*
International Search Report and Written Opinion; In re: PCT International Application No. PCT/CN2010/000740; Dated: Aug. 19, 2010; Applicant: Shanghai Jiao Tong University, et al. (English Translation Attached).
Ohta, Susumu, et al.; "Midkine Is Expressed During Repair of Bone Fracture and Promotes Chondrogenesis"; Journal of Bone and Minteral Research; vol. 7, No. 7 (1999); pp. 1132-1144.
Supplementary Search Report received in European application No. 10779997 dated Oct. 4, 2012 (6 pages).

* cited by examiner

*Primary Examiner* — Xiaozhen Xie
(74) *Attorney, Agent, or Firm* — Foley & Lardner LLP

(57) ABSTRACT

The applications and medical devices of Midkine in the field of biotechnology are described in this invention. This invention describes the applications of the protein as follow in (a) or (b) in preparing drugs for promoting cartilage growth or treating cartilage diseases, the protein as a growth factor for promoting chondrocyte proliferation, or medical devices containing this protein: (a) the protein whose amino acid sequence is shown as SEQ ID NO.1; (b) the proteins whose amino acid sequence have at least 60% homology comparing with amino acid sequence described in (a). The present invention is different from the present knowledge of MK and its related proteins. The experimental results demonstrated that MK promotes proliferation of three types of chondrocytes and is used for preparing drugs for treating cartilage disease. It may provide new therapy for treating cartilage diseases clinically, and new technology for expansion of chondrocytes in vitro for cartilage tissue engineering.

7 Claims, 5 Drawing Sheets

SEQUENCE LISTING

```
<160> NUMBER OF SEQ ID NOS: 9

<210> SEQ ID NO 1
<211> LENGTH: 122
<212> TYPE: PRT
<213> ORGANISM: Homo sapiens

<400> SEQUENCE: 1

Met Lys Lys Lys Asp Lys Val Lys Lys Gly Gly Pro Gly Ser Glu Cys
1               5                   10                  15

Ala Glu Trp Ala Trp Gly Pro Cys Thr Pro Ser Ser Lys Asp Cys Gly
            20                  25                  30

Val Gly Phe Arg Glu Gly Thr Cys Gly Ala Gln Thr Gln Arg Ile Arg
        35                  40                  45

Cys Arg Val Pro Cys Asn Trp Lys Lys Glu Phe Gly Ala Asp Cys Lys
    50                  55                  60

Tyr Lys Phe Glu Asn Trp Gly Ala Cys Asp Gly Gly Thr Gly Thr Lys
65                  70                  75                  80

Val Arg Gln Gly Thr Leu Lys Lys Ala Arg Tyr Asn Ala Gln Cys Gln
                85                  90                  95

Glu Thr Ile Arg Val Thr Lys Pro Cys Thr Pro Lys Thr Lys Ala Lys
            100                 105                 110

Ala Lys Ala Lys Lys Gly Lys Gly Lys Asp
        115                 120

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gaatggctga cctgacctga ta                                              22
```

```
<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggcgtctgac tcacaccaga ta                                             22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gggcaagaca gtcatcgaat a                                              21

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atgtccattc cgaattcct                                                 19

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tggcagacca gtacccgcat ct                                             22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tctttcttgt gctgcacgcg c                                              21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gaggcatcct gaccctgaag                                                20
```

```
<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
catcacaatg ccagtggtac g                                               21
```

USE OF MIDKINE PROTEIN AND THE PROTEIN-CONTAINING MEDICAL DEVICE

SEQUENCE LISTING

The instant application contains a Sequence Listing which has been submitted in ASCII format via EFS-Web and is hereby incorporated by reference in its entirety. Said ASCII copy, created on Dec. 28, 2012, is named 91274113.txt and is 3,268 bytes in size.

FIELD OF THE INVENTION

This invention relates to a protein in the field of biotechnology and medical devices containing the protein, specifically to the use of recombinant Midkine protein and medical devices containing the protein.

BACKGROUND OF THE INVENTION

Cartilage is an avascular connective tissue, distributed in all parts of the body. It consists of cartilage cells and extracellular matrix which is secreted and maintained by cartilage cells. According to the morphological criteria and the content of collagen and elastin, cartilage can be divided into three categories: hyaline cartilage, such as the nasal septum, articular cartilage, trachea and bronchi; elastic cartilage, such as ear and epiglottis; and fibrocartilage, such as meniscal cartilage and intervertebral disc. Naumann, A, etc. published a report entitled "Immunochemical and mechanical characterization of cartilage subtypes in rabbit" in the "Journal of Histochemistry and Cytochemistry" (2002(50):1049-1058), which comments that hyaline cartilage contains mostly type II collagen, elastic cartilage contains mainly elastin and fibrocartilage contains mostly type I collagen.

Articular cartilage and the intervertebral disc play an important role in the systemic motion. The homeostasis of extracellular matrix of articular cartilage and intervertebral disc depends on their anabolic and catabolic metabolism in articular cartilage and intervertebral disc. When the balance of cartilage matrix breaks, cartilage-matrix gradually loses its normal physiological functions, eventually leading to joint and disc disease, such as osteoarthritis and intervertebral disc degeneration. As the cartilage has very limited ability to repair itself, a variety of clinical methods and experimental methods which are used to improve the cartilage regeneration can not efficiently repair the damaged cartilage to meet clinical needs.

Biological treatment of damaged cartilage may replace chronic traditional treatment methods and reconstruction surgical methods. However, these biological treatment methods rely on the use of growth factors. At present, many cytokines are in development, specifically for cell growth, differentiation and cartilage matrix synthesis, and so on. These include fibroblast growth factors (FGFs), insulin-like growth factor-1 (IGF-1), transforming growth factor-β (TGF-β) cartilage-derived morphogenetic proteins (CDMPs), bone morphogenetic proteins (BMPs) and connective tissue growth factor (CCN2/CTGF). Shida, J, etc. published a report entitled "Regulation of osteoblast, chondrocyte and osteoclast functions by fibroblast growth factor (FGF)-18 in comparison with FGF-2 and FGF-10" in the "Journal of Orthopaedic Research" (2002(277):493-7500). It comments that when FGF-2 and FGF-18 are given by intra-articular injection, FGF-2 can not only promote the increase of the articular cartilage of the young rats, but also promote the proliferation of mesenchymal cells and cover the articular surface. Ellsworth, J. L, etc. published a report entitled "Fibroblast growth factor (FGF)-18 is a trophic factor for mature chondrocyte and their progenitors" in the "Osteoarthritis and Cartilage" (2002(10):308-320). It comments that expression of FGF-18 by adenovirus promoted the formation of cartilage cells around the virus injection site, but had no effect on the mouse ear elastic cartilage. Therefore, there is a need to discover a growth factor which can promote the growth of cartilage tissue in vivo, rather than promote the proliferation of other cell types.

Cartilage tissue engineering is a technology used for cartilage disease and injury. Autologous chondrocyte transplantation (ACT) technology has been used in clinical treatment for craniofacial and joint cartilage damage. So far, ACT technology has cured more than 12,000 patients with full-thickness cartilage defects worldwide. The main challenge of cartilage tissue engineering is to obtain sufficient cartilages cells to fill the cartilage defect site. Due to the limited number of cartilage cells in vivo, only 5% to 10% of chondrocytes in cartilage tissue, in vitro expansion is required before clinical use. Brittberg, M, etc. published a report entitled "Treatment of deep cartilage defects in the knee with autologous chondrocyte transplantation" in the "New England Journal of Medicine" (1994(331):889-895). It comments that chondrocyte are mainly isolated from hyaline cartilage of joint and elastic cartilage of ear, and cultured in vitro. Currently chondrocytes are cultured in vitro in monolayer with serum-containing medium. Although this method is very effective in expansion of chondrocytes, chondrocytes often differentiate into fibroblasts and lose the chondrocyte characteristics. The first to fourth passages of subcultured chondrocytes maintain their chondrocyte characteristics when they are cultured in high-density or transplanted into animals (this process is known as re-differentiation). Therefore, the ability of re-differentiation is closely related to the number of passages in culture. At present, a variety of growth factors such as FGF-2, TGF-β, BMP-2 and IGF-1 have been applied to chondrocyte culture in vitro for promoting chondrocyte proliferation, reducing differentiation and re-differentiation. Currently, it is an important goal to search for an ideal chondrocyte growth factor for chondrocyte culture in vitro. This ideal growth factor can promote the amplification of three kinds of cartilage cells and maintain their characteristic gene expression profiles and the synthesis of the cartilage-specific matrix in limited subculture.

Midkine (MK) is a member of pleiotropic factor/midkine family, it was originally described as a factor that is produced by retinoic acid, and heparin-binding neurotrophic factor which regulates growth. MK is highly expressed in the brain and other tissue in the second trimester, and decreased after birth. In adult animals, MK is strictly expressed with high level of transcription in the small intestine, and low expression in other tissues. Ohta, S, etc. published a report entitled "Midkine is expressed during repair of bone fracture and promotes chondrogenesis" in the "Journal of Bone and Mineral Research" (1999(14):1132-1144), which finds that mouse ATDC5 cells transfected with MK gene can promote cartilage matrix synthesis. But the research also pointed out that not all high expression of MK-transfected cell line can produce cartilage matrix. In cultured ATDC5 cells, MK did not promote the synthesis of cartilage matrix. Dreyfus, J, etc. published a report entitled "HB-GAM/pleiotrophin but not RIHB/midkine enhances chondrogenesis in micromass" in the "Experimental Cell Research" (1998(241):171-180), which finds that, similarly, addition of exogenous MK can not promote mesenchymal cells from chicken embryos in micromass culture to synthesis cartilage matrix. These results demonstrate that MK does not promote chondrocyte growth and differentiate in vitro. However, the inventors discovered that MK promoted the growth of three different cartilage tissues in normal animals and that addition of exogenous MK protein to single layer culture promoted proliferation of the three types of chondrocytes without changing the expression profile of chondrocyte specific genes.

SUMMARY OF THE INVENTION

The purpose of this invention is to overcome the shortcomings of existing technology and provide the use of the recombinant human midkine (rhMK) and medical devices containing rhMK. This invention is completely different from the prior understandings of MK and this family of proteins. Experimental results show that rhMK is effective in promoting proliferation of three categories of cartilage in vitro and in vivo. It can be used to treat cartilage diseases. Meanwhile, rhMK can also be used for cartilage tissue engineering in amplification of cartilage cells in vitro.

The present invention describes the use of a protein as in (a) or (b) in preparing drugs for promoting cartilage growth and treatment of cartilage diseases.

(a) The amino acid sequence of the protein is shown as SEQ ID NO.1; (b) Proteins whose amino acid sequence are at least 60% homologous with (a).

The term of "cartilage" includes hyaline cartilage, elastic cartilage, or fibrocartilage.

The term of "cartilage disease" includes traumatic cartilage damage, osteoarthritis, intervertebral discs degeneration, cartilage dysplasia, achondroplasia, costal cartilage inflammation or recurrent polychondritis.

The term of "traumatic cartilage damage" includes articular cartilage damage, full-thickness articular cartilage damage or traumatic damage of intervertebral disc cartilage.

The use of protein described as follows in (a) or (b) as a chondrocyte growth factor:

(a) The amino acid sequence of the protein is shown as SEQ ID NO.1; (b) Proteins whose amino acid sequence are at least 60% homologous with (a).

The term of "chondrocyte growth factor" describes a growth factor that can amplify chondrocytes in vitro.

The term of "chondrocyte" means hyaline chondrocyte, elastic chondrocyte or fibro chondrocyte. In certain embodiments, the term of "usage" in the present invention means the usage of the protein whose amino acid sequence is as the same as SEQ ID NO.1 in the preparation of chondrocyte growth factor drugs.

In one aspect, the present invention discloses a pharmaceutical composition containing the protein described in (a) or (b) as an active ingredient and pharmaceutically acceptable carrier or excipient:

(a) The amino acid sequence of the protein is shown as SEQ ID NO.1; (b) Proteins whose amino acid sequence are at least 60% homologous with (a).

In another aspect, the present invention also discloses medical devices containing the protein (a) or (b):

(a) The amino acid sequence of the protein is shown as SEQ ID NO.1; (b) Proteins whose amino acid sequence are at least 60% homologous with (a).

The medical device could be stent.

On the other hand, the present invention discloses a method in which the described protein is an active ingredient that promotes the formation of cartilage and treatment of the related disease and clinical symptoms. This method comprises the administration of a curative dose of the described proteins.

In another aspect, the present invention provides a therapeutic method to treat diseases or symptoms through promoting regeneration of cartilage tissue. The method comprises a step in which a stent containing a curative dose of the described proteins is administrated.

In another aspect, the present invention provides a preventive method to treat diseases or symptoms through promoting regeneration of cartilage tissue. The method comprises a step in which a stent containing collagen IIa with the therapeutic dose of the described protein.

In another aspect, the present invention provides a method of promoting cartilage formation, which comprises a step of giving a stent. The stent contains collagen IIa with the therapeutic dose of the described protein.

The present invention has the following benefits: The present invention completely differs from pre-existing technologies about MK and related proteins. The experiments demonstrated that MK promoted proliferation of three types of chondrocytes in vivo. MK can be used to make drugs for treating cartilage diseases, which provide new option for clinical treatment of cartilage diseases. At the same time, MK can be applied to expand chondrocytes in vitro in cartilage tissue engineering.

DETAILED DESCRIPTION

Figure 1:
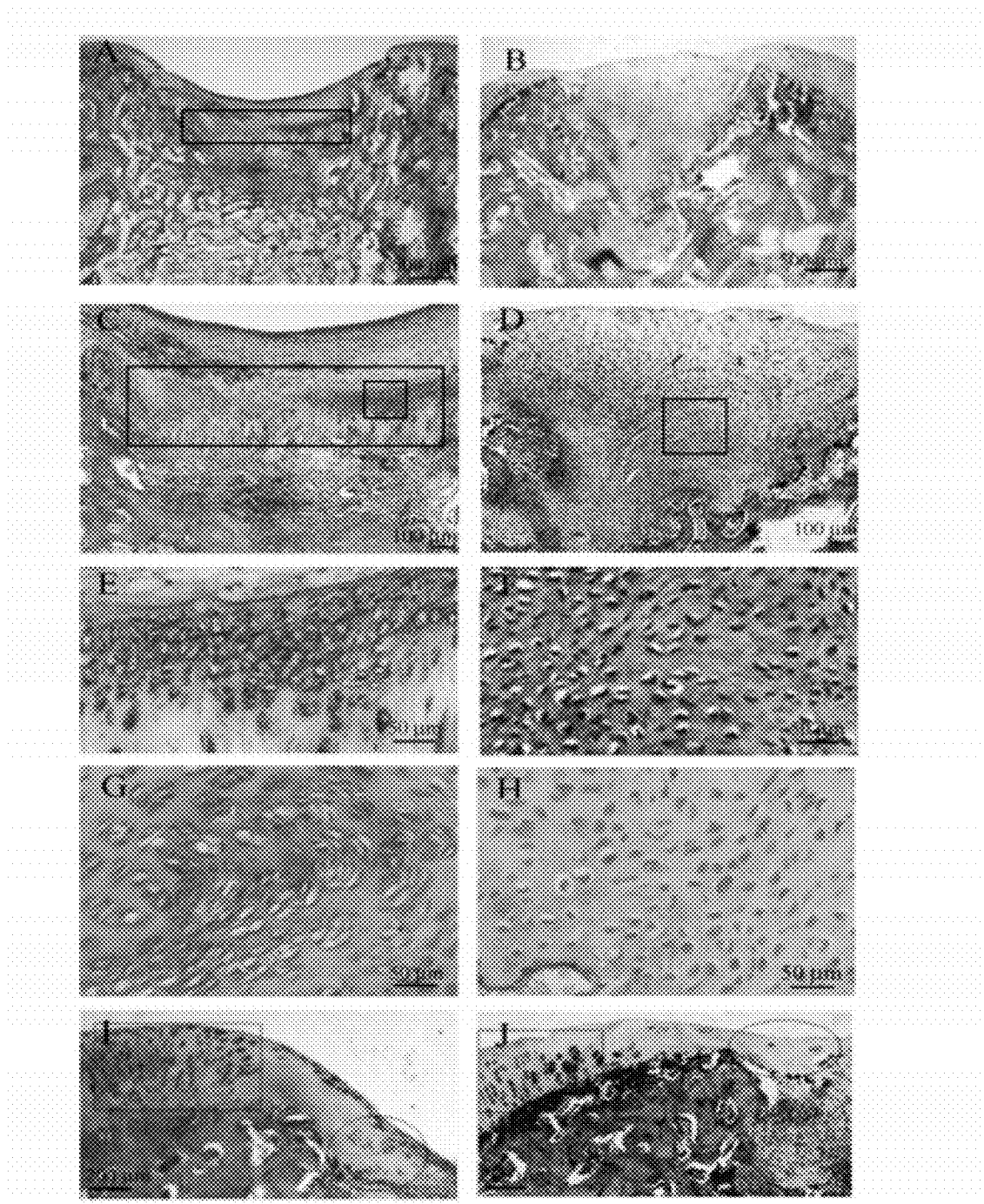
FIG. 1, Histological evaluation of rhMK treated full-thickness defects of rabbit knee articular cartilage. Four weeks after the defect model created.

The following examples combined with the drawings will be used to illustrate the invention further. The embodiments were implemented in the premise of the technical scheme of the invention, described the detailed implementation methods and processes, but the scope of the present invention is not limited to the following examples. If specific conditions in experimental methods are not given in the following examples, the conditions are usually in accordance with the conventional conditions, or in accordance with the manufacturers recommended conditions.

In the present invention, the term "cartilage" refers to any cartilage in human or animal, including but not limited to: articular cartilage, hyaline cartilage, meniscus cartilage and elastic ear cartilage.

In the present invention the protein we claimed refers to protein (a) or (b):

(a) The amino acid sequence of the protein is shown as SEQ ID NO.1; (b) Proteins whose amino acid sequence are at least 60% homologous with (a) and have the ability to promote chondrocyte proliferation.

In the present invention, the protein we claimed is the follows: substance that has the protein's amino acid sequence described as SEQ ID NO.1; the rhMK and its mutants, functional active fragment or analogs; vectors coding protein contained the amino acid sequence of SEQ ID NO.1, such as DNA vector (plasmid or virus). The above functional active fragments or analogues can be created by addition, insertion, modification, replacement or omission of one or more amino acid residues of the amino acid sequence of SEQ ID NO.1.

The term "analogue" also includes chimeric proteins, fusion proteins, anti-idiotypic antibodies, and their precursors and other functional equivalents or stimulants, and synthetics which mimics the activity of rhMK.

The term "mutants" referred to mutants of rhMK which has changes in amino acid sequence of SEQ ID NO.1. The mutants have enhanced activity and/or changed stereo-selectivity compared with natural wild-type of natural MK protein. Amino acid sequences mutants of the natural protein can be prepared by introducing the appropriate nucleotide changes of nucleotides in the present invention or by synthesizing the required peptide in vitro. These mutants include the deletion, insertion, or replacement of the amino acid sequence residues of rhMK. The mutant proteins may be produced by combination of deletion, insertion, or replacement of the rhMK nucleotide sequences in the vectors.

In the present invention, the field we claimed also includes MK protein analogs and different modifications during or after their synthesis. These modifications, for example, biotinylation, benzylation, glycosylation, acetylation, phosphorylation, derivation of known protected/closed groups, cutting action by proteolysis, connection to an antibody molecule or other cellular ligands, can be used to increase the stability and/or biological activity of MK protein in the present invention.

Formulation

The pharmaceutical formulation in the present invention or the formulations containing the protein are described in the present invention. The proteins could be mixed with one or more pharmaceutically acceptable carriers or excipients to meet the needs of various administration methods, such as tablets, capsules, powders, granules, syrup, solution, oral liquid, spiritus agents, tinctures, aerosols, powders, injections, sterile powder for injection, suppository, etc. . . .

"Pharmaceutically acceptable" components are suitable for human beings and/or animals, and without excessive adverse side effects (such as toxicity, irritation and allergic reaction). It means that the benefit/risk factor is reasonable. "Pharmaceutically acceptable carriers" are the acceptable solvents, suspending agents or excipients used in pharmacy or foods for the purpose of delivery of the proteins of the present invention to the animals or human beings. The carriers could be liquids or solids.

The proteins of the present invention could be administered via the routes like oral, intravenous, intramuscular or subcutaneous.

The formulations for parenteral administration include injection and sterile lyophilized powder. Both are mixtures of drugs and one or several pharmaceutically acceptable carriers or excipients for parenteral administration. The solvents include sterile water, ethanol, glycerol, propylene glycol and polyethylene glycol. Besides, bacteriostats (e.g., benzyl alcohol, butyl paraben, thiomersalate), isoosmotic adjustment agents (e.g., sodium chloride, glucose), suspending agents (e.g., sodium carboxymethylcellulose, methylcellulose), solubilizers (e.g., Tween-80, phosphatidylcholine), antioxidants (e.g., Vitamin E, Vitamin C, sodium pyrosulfite) and stuffing bulking agents (e.g., maltose, mannitol) are needed.

In a practical application of the invention, we offer an artificial support which would promote cartilage formation, and such support would effectively bind the said protein.

The support could be in the form of a 3 dimensional matrix or plane (e.g., continuous film or gelatin). Such matrix structure could be produced with fiber or other suitable materials, and form the required 3 dimensional shape through spinning processes including weaving, knitting, interweaving or non-interweaving, melt blowing, coherence). Such matrix structure could also exist in other forms, like spongy or foamy ones.

The suitable material for the support would be adjusted to biodegradation, and would not inhibit cell growth or proliferation. The material would not cause untoward effects to patients, and would be sterilized.

Thus, the suitable materials would include biodegradable polyester, like PLA, PGA, polydioxanone, polyhydroxyalkanoates (e.g., ICI) and hyaluronic acid derivatives (e.g., HYAFF). More suitable materials would include those published in patent applications WO91/13638 and WO97/06835 as referenced, like hydrophilic polyurethane, PEEK, polyethylene oxide, polyether polyamide, carboxymethylcellulose, vinyl acetate copolymer, polybutadiene, styrene-butadiene-styrene segmented copolymer, etc.

Other support materials are collagen based substances, e.g., crosslinking collagen/elastin materials, crosslinking collagen produced from acid soluble type I ox collagen, and collagen gel (like those substances with trade names of COLLASTAT and COLETICA). Both natural and recombinant collagens (e.g., collagen IIa) are applicable.

In this invention we also provide modified or chimeric restructured fibrous collagen (referred to as "modified collagen" here). When combined with the said protein, it could increase the performance and stability of the protein. Another example would be the integration of the said protein into other extracellular compositions (e.g., fibronectin connecting protein, collagen IV, ECM binding molecules or sequences like heparin binding domain), in a way similar to domain remodeling. Please refer to WO97/08311, the contents of which have been integrated into the patent application as reference.

In certain embodiments, we also provide a bone-substitute composition containing a synthetic material. Such synthetic material could be any one of the aforementioned support materials, or any crystal binding the said protein (e.g., apatite, like hydroxyapatite).

In our invention, the said protein is provided in the form of gel as a support material. Such gel consists of thrombin, fibrinogen, factor XIII or other gel-crosslinking transglutaminase.

In certain embodiments, we also provide a support material which would enhance cartilage tissue formation and growth. Such support material is made of collagen type IIa, or covered with collagen type IIa.

We provide a support material containing collagen type IIa which could release the said protein in a well-controlled manner. Thus, the targeting property of the MK is improved. In the detailed application scheme, the protein is released through normal cell activities and/or MK releasing devices/ drugs. The protein could also be released through the degradation of the support material.

In this invention we intend to facilitate the interaction between the protein and its target cells, at the defect sites. The target cells would thus be induced to express and synthesize cartilage compositions and result in the recovery of damaged parts of the cartilage tissue.

According to technologies available at the current time, this invention further provides a method of producing the cartilage growth stimulating support material, which is covered by the said protein.

Applications of the Invention

In this invention we have disclosed methods of stimulating cartilage reformation with the protein referred to in the invention as the active ingredient to relieve or treat diseases or clinical symptoms. Such methods include the administration of the said protein with effective dose.

The terms "effective dose" and "curative dose" both refer to a dose which is large enough for the curative effects to take place. The effective dose could be given in single or multiple times.

The effective dose of the protein can change based on the delivery mode and severity of the disease. For most large mammals, total dose of the protein is about 0.01~1000 mg per day. Clinical dose range for adult is about 0.01~200 mg per day, preferable for 0.05~100 mg per day.

This invention also provides a method for relieving or curing disease or symptoms through promoting cartilage formation. This method includes the use of a scaffold which contains effective dose of MK.

This invention also provides a method for relieving or curing disease or symptoms through promoting cartilage formation. This method includes the use of a scaffold which is made of collagen IIa containing an effective dose of the said protein.

The clinical symptoms and diseases remitted or treated by the therapy described in this invention include degenerative joint diseases like osteoarthritis (OA), lumbar disc herniation, meniscus tear, and Hunter-Thompson dyschondroplasia. The therapy is also used to treat cartilage diseases of joints, include the cartilage diseases limited in cartilage or subchondral bone caused by trauma and/or degeneration.

This invention also presents the applications of the described protein as a chondrocyte growth factor. The protein can be used on promotion of chondrocyte proliferation, also can be used on cartilage tissue engineering to produce artificial cartilage singly or combining with insulin-like growth factors, fibroblast growth factors, vascular endothelial cell growth factors, and bone morphogenetic protein, see details on reference "Chung C, Burdick JA. Adv Drug Deliv Rev. 2008 14; 60(2):243-62; Changhong Chen, Chen Wang International orthopaedic magazine. 2006(2)117~119".

Examples

The details of this invention are described in the following specific examples. These examples are just used to explain this invention rather than define its application range. If no details are given, experimental methods are carried out according to general protocols or instructions from manufacturers. The meanings of professional words or scientific phrases used in this text are the same as used by professionals in this field.

The experiment animals in examples:

C57BL/6J mice and Sprague-Dawley (SD) rats (purchased from SLAC Laboratory Animal Center, Shanhgai, China) were fed in animal cages with filtered air supply. The temperature and humidity were kept at 23±5° C. and 55±5%. The bodyweight of New Zealand white rabbits (purchased from Experimental Animal Center, Chedun, Shanghai) were 2.0~2.5 kg.

Example 1

Preparation of Recombinant Human Midkine (rhMK)

DNA sequences encoding human MK mature protein (GenBank NM_001012334) was linked to pET30a+ vector (Novagen, USA) according to our published report 《 Zhang Z, Du L, Xiang D, Zhu S, et al. J Zhejiang Univ Sci B, 2009, 10: 79~86》, and transformed to $E.\ coli$ to express the protein. The recombinant human MK protein was purified using ion-exchange chromatography. The purity of the prepared protein is >98% by reverse phase HPLC analysis. The concentration of endotoxin was <0.3 EU/ug protein. The bioactivity of purified rhMK was analyzed by NIH3T3 proliferation assay.

Example 2

The Effect of Recombinant Human MK on Cartilage of Health Mice, Rats and Rabbits Method. 8-weeks-old male C57BL/6J mice were injected subcutaneously with recombinant human MK (rhMK) or control saline. The injection volume was 0.5 ml, given daily for a week. The mice were grouped (3 animals per group): Saline (NS) group, rhMK groups injected with various dosages at 10, 33, 100, 300, 900 μg/kg. Rats were injected with saline or rhMK (175 μg/kg) daily for a week. Rabbits were injected with saline or rhMK (92.5 μg/kg) daily for two week.

Histological observation and evaluation. The knee joint tissues of all mice and rats were fixed in 10% (v/v) formalin for 1 day, the tissues of rabbits were fixed for 2 days. The fixed tissues were subjected to demineralization in liquid (7% $AlCl_3.6H_2O$, 5% methanoic acid, 8.5% HCl) 4 days for mouse and rats issues, and 10 days for rabbit tissues. The demineralized tissues were subjected to dehydration by gradient ethanol, and treated for transparency by xylene, and embedded in wax. Tissue sections were prepared by the paraffin slicing machine (Laica), and stained with hemotoxylin/eosin or Safranine O/fast green staining. Slides were observed under microscope and analyzed. The thickness of cartilage tissues were measured by the vernier caliper on microscope. Three tissue sections from each sample were measured and analyzed statisticaly. The distance between surface of cartilage to subchondral tide line was measured at ½ position of femoral condyle to denote the thickness of knee-joint cartilage. The thickness of cartilage at central part of ears was measured to denote the thickness of ear elastic cartilage. The distance between out surface of annulus to nucleus of the intervertebral disc was measured to denote the thickness of thoracic intervertebral disc (T2-3).

Result. The effect of rhMK on growth of normal cartilage tissue. For investigating the biological function of rhMK on cartilage tissue in vivo, we expressed and purified recombinant human MK (rhMK). According to the analysis of the cartilage tissue sections at 15 days post rhMK injection, we discovered that the protein significantly promoted the growth of mouse knee-joint articular cartilage, ear elastic cartilage, and fibro cartilage of intervertebral disc (Table 1). The effective dose that promoted the growth of all three categories of cartilages in mice is 300 μg/kg/day. In three tissues, the articular cartilage and ear elastic cartilage are more sensitive to rhMK, the minimum effective dose is 10 ng/kg/day. The mice of all groups did not generate redundant cartilage tissue around thighbone. We conclude that rhMK promote tissue regeneration of the three categories of cartilage.

hole was 3 mm in diameter and 4 mm in depth. The wound was closed with 4-0 lines. 400,000 units penicillin was injected daily for one week to prevent the wound site infection. 24 hours after surgery, normal saline or rhMK was injected into the knee articular cavity. The injection volume

TABLE 1 rhMK promotes the cartilage growth of normal mouse

| Thickness of cartilage(μm) | rhMK (μg/kg) | | | | | |
|---|---|---|---|---|---|---|
| | 0 | 10 | 33 | 100 | 300 | 900 |
| Femoral condyle | 138.6 ± 8.0 | 152 ± 2.7 | 156.4 ± 8.1* | 172.4 ± 11.1* | 195.3 ± 9.9* | 200.0 ± 7.0** |
| Ear elastic cartilage | 37.3 ± 0.9 | 47.6 ± 4.7* | 46.2 ± 5.6* | 48.9 ± 5.5* | 58.5 ± 19.6* | 51.6 ± 5.6** |
| Intervertbral disc (T2-3) | 163.3 ± 14.8 | 193.8 ± 25.2 | 206.2 ± 29.4* | 193.8 ± 3.1* | 200.7 ± 17.2* | 217.1 ± 6.0** |

Mice were injected subcutaneously with rhMK daily for one week. The tested dosages of the protein is presented in the table 1. Three mice per group were analyzed. The data in the table are denoted as mean ± SD. Each experiment was repeated three times.
* and ** denote significant differences (*$P < 0.05$ and **$P < 0.01$) between the indicated group and 0 dose group by Student t-test.

To verify the results of rhMk in mice, we performed the same experiments in vivo using commonly used laboratory animals, rat and rabbit. Rats were injected subcutaneously with rhMK at 175 μg/kg/day for one week, and rabbits was injected subcutaneously 92.5 ug/kg/day for two weeks. By observation of tissue sections at the 15th day after administration of recombinant protein, the rhMK was demonstrated significantly promoting the growth of four categories of cartilage tissues, including articular cartilages, ear cartilages, tracheal cartilages, and cartilages of intervertebral disc (Table 2).

The injection dose of rhMK: mice was injected subcutaneously 300 μg/kg daily for a week; rats were injected 175 μg/kg daily for a week; and New Zealand rabbits was injected 92.5 μg/kg daily for two weeks. Three animals per group were analyzed.

was 0.5 ml, three times a week for 2 weeks. rhMK was injected into one side of the rabbit knee joint, the other side was injected with saline as control. The rabbits were kept in cages and moved freely without fixation of the injured knees. After 2, 4, 6 and 12 weeks, rabbits were sacrificed. Cartilage tissues of the knee joint were removed for routine biopsy. The tissue sections were prepared for H&E, and fast green—Safranin O staining. The histological observation and evaluation were conducted under microscope.

Results. The left column in FIGS. 1 (A, C, E, G and I) is rhMK treated tissue sections and the right column (B, D, F, H and J) is the saline treated tissue sections. H&E staining is used in Figure A, B, C, D, E, F, I and J. Fast green—Safranin O staining is used in FIGS. 1G and H. The rectangle indicated area in FIG. 1A is enlarged and shown in Figure C. The small rectangle in FIG. 1C is enlarged and shown in FIG. 1E. The

TABLE 2 rhMK promotes the cartilage growth of different normal animals

| Cartilage thickness (mm) | Mouse | | Rat | | New Zealand rabbit | |
|---|---|---|---|---|---|---|
| | Control | rhMK | Control | rhMK | control | rhMK |
| Femoral condyle | 138.6 ± 8.0 | 195.3 ± 9.9* | 172.3 ± 8.2 | 262.7 ± 54.4* | 401.8 ± 8.3 | 611.5 ± 6.4** |
| Ear | 37.3 ± 0.9 | 58.5 ± 19.6* | 63.2 ± 15.5 | 106.6 ± 3.4** | 407.9 ± 9.3 | 605.4 ± 5.4** |
| Trachea | 83.7 ± 0.9 | 114.5 ± 18.0* | 186.7 ± 6.9 | 246.4 ± 9.1** | 353.6 ± 9.1 | 495.2 ± 6.5** |
| Intervertbral disc (T2-3) | 163.3 ± 14.8 | 200.7 ± 17.2* | 422.1 ± 43.3 | 659.4 ± 40.8** | 1191.2 ± 48.0 | 1516.4 ± 54.0** |

Each experiment was repeated three times. The data in the table are denoted as mean ± SD.
* and ** denote significant differences (*$P < 0.05$ and **$P < 0.01$) between the indicated group and 0 dose group by Student t-test.

Example 3 rhMK Treats Full-Thickness Cartilage Defect of Rabbit Knee Joint

Method. 2-month-old male New Zealand white rabbits (2.0~2.5 kg weight) were anesthetized with 3% pentobarbital sodium (30 mg/kg) by ear vein injection. After anesthesia, prepare the skin on both sides of the knees were prepared for sterilization. With conventional surgical sterilization and under sterile conditions, the inner side of knees was cut to expose the femoral condyle surface. The full-thickness cartilage injury was made on the femoral condyle surface for both sides of the rabbit knees using an electrical drill. The cartilage rectangle in FIG. 1D is enlarged and shown in FIG. 1F. The rectangles shown in FIGS. 1I and J are the remaining cartilage near the site of injury; and the circles indicates the newly formed chondrocytes (FIG. 1I) are originated from the residual chondrocytes, which is not observed in FIG. 1J, the side used saline as control treatment.

The most significant effect of rhMK was observed in promoting the formation of new chondrocytes in the injury area. 4 weeks after surgery, the injury sites were filled with new tissues completely in both rhMK and saline treated sides (FIGS. 1A and 1B). Importantly, in rhMK treated side, new chondrocytes appeared in palisade in the injury site (FIG. 1C). The new cells appeared in clusters as hypertrophic chondrocytes which resided in cartilage lacunae (FIG. 1E). They were stained positive with Safranin O, a dye specific for proteoglycan of cartilage matrix (FIG. 1G). However, in the saline treated side, the new cells were irregular in shape and scattered in arrangement (FIG. 1F), did not form lacunae (FIG. 1F); and stained only slightly with Safranin O (FIG. 1H). It was also found that, in rhMK treated side, there were many live chondrocytes in the remnants of cartilage surrounding the injury site (FIG. 1I rectangular box area). These chondrocytes grew into the injury site, and formed a string of new chondrocytes (FIG. 1I circle). In contrast, the knee joint of the control side treated with saline, this phenomenon was not observed (FIG. 1J rectangular and circular box area). Therefore, we conclude that rhMK injected locally promotes the formation of new cartilage tissue in full-thickness injury of knee articular cartilage. The newly formed cells are articular chondrocytes. At the minimum, part of the new cartilage is regenerated from the residual articular cartilage around the injury site.

Figure 2:
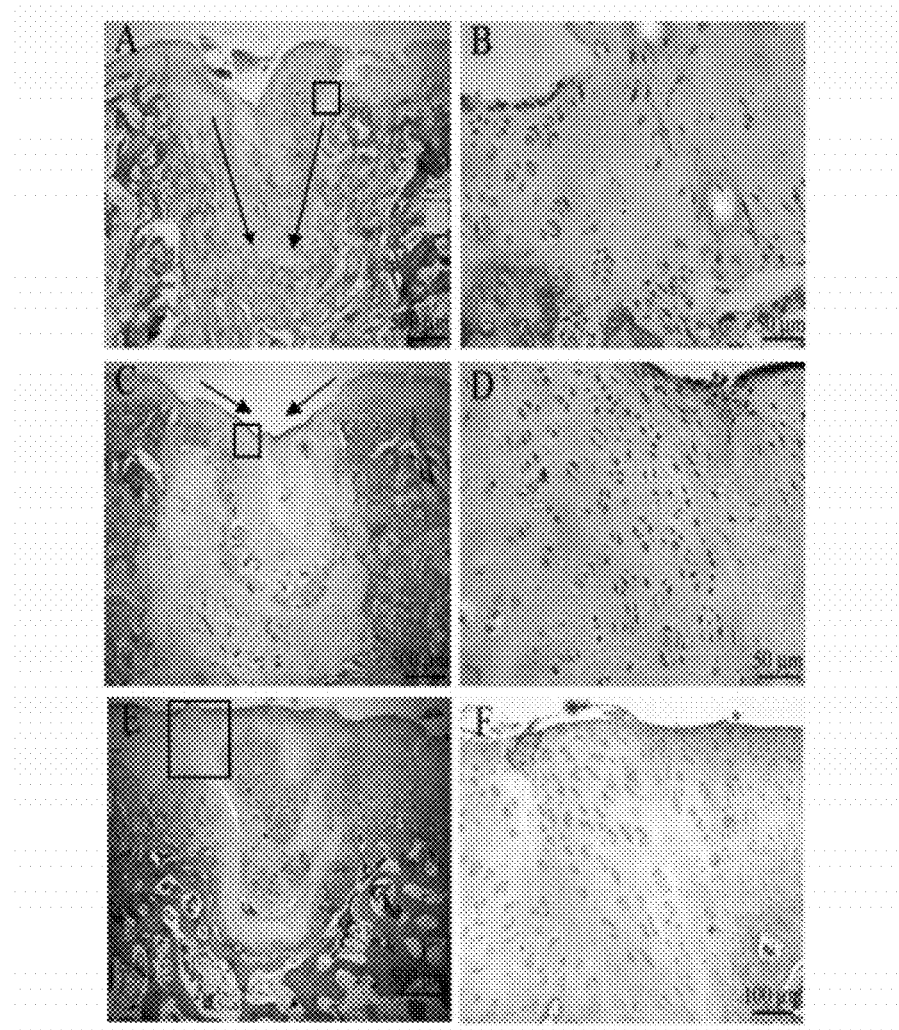
FIG. 2, Histological evaluation of rhMK treated full-thickness defects of rabbit knee articular cartilage. Various time points after the defect model created.

The histology of knee cartilage samples taken at different time points was analyzed to observe the repair role of rhMK revealed temporally (FIG. 2). rhMK was shown promoting the repair of rabbit knee full-thickness injuries with regenerated chondrocytes 2 weeks (FIGS. 2A and B), 4 weeks (FIGS. 2 C and D), and 12 weeks (FIGS. 2 E and F) after the knee surgical operation creating the damage model. The rectangle in FIGS. 2 A, C and E marks the areas which are enlarged and shown in FIGS. 2 B, D and F, respectively. In FIGS. A and C, arrow points to the chondrocytes which are growing into the injury site. At 2 weeks after the surgery, although the central area of injury was filled with fibrous cells, incomplete hyaline cartilage layer appeared forming the cylindrical repair cartilage layer (FIG. 2A). The new cartilage layer contained the typical chondrocytes which resided in clusters in specific cartilage lacuna (FIG. 2B). At 4 weeks after the surgery, the complete cylindrical repair cartilage layer formed and appeared as a "U" shape (FIGS. 2C and 2D). At 12 weeks after the surgery (FIG. 2E), the injury was completely repaired by articular cartilage and the newborn bone marrow filled the center of the injury site. And, marrow sinus and subchondral bone were formed. The tidal line was fully restored (FIG. 2E). The new cartilage surface was covered by regenerated chondrocytes resided in cartilage lacunae (FIG. 2F). The rate of recovery in the rhMK treated side of this cartilage damage model is 72.2% (18 samples, 13 recovered), compared with no recovery in the control sides injected with saline ($P<0.01$ by Fisher's exact test). Therefore, in rabbit knee cartilage full-thickness injury model, the cellular characteristics of repaired tissue in rhMK treated group was completely different from saline control group, the former was filled with regenerated chondrocytes, but the latter was filled with chondrocyte-like cells.

Example 4 rhMK Treats Partial-Thickness Cartilage Defect of Adult Rabbit Knee Joint

Method. 9~10-month-old male New Zealand white rabbits (3.0~3.5 kg weight) were anesthetized with 3% pentobarbital sodium (30 mg/kg) by ear vein injection. After anesthesia, the skin was prepared on both sides of the knees. With conventional surgical sterilization and under sterile conditions, the inner side of the knees was cut to expose the femoral condyle surface. A hand-drill was used to make a partial-thickness cartilage injury of 3 mm in diameter on the femoral condyle surface. The partial-thickness injury was created by the criterion of no bleeding in the injured cartilage hole. The wound was sutured with 4-0 lines. 400,000 units penicillin was injected every day for one week to prevent the wound site infection. 24 h after the surgery, normal saline or rhMK was injected into the knee-articular cavity. Partial-thickness cartilage damages were created on both rabbit knees. One knee received 0.5 ml saline as control side, while 0.5 ml rhMK was given into the other knees as treatment side. The injections were given three times a week, for 2 weeks totally. The rabbits were kept in cage and allowed freedom of movement without the knee fixed. 4 and 9 weeks after the surgery, rabbits were sacrificed. The knee-joint cartilage tissues were removed for routine biopsy, H&E, and toluidine blue staining, and their histological changes were analyzed under microscope.

Figure 3:
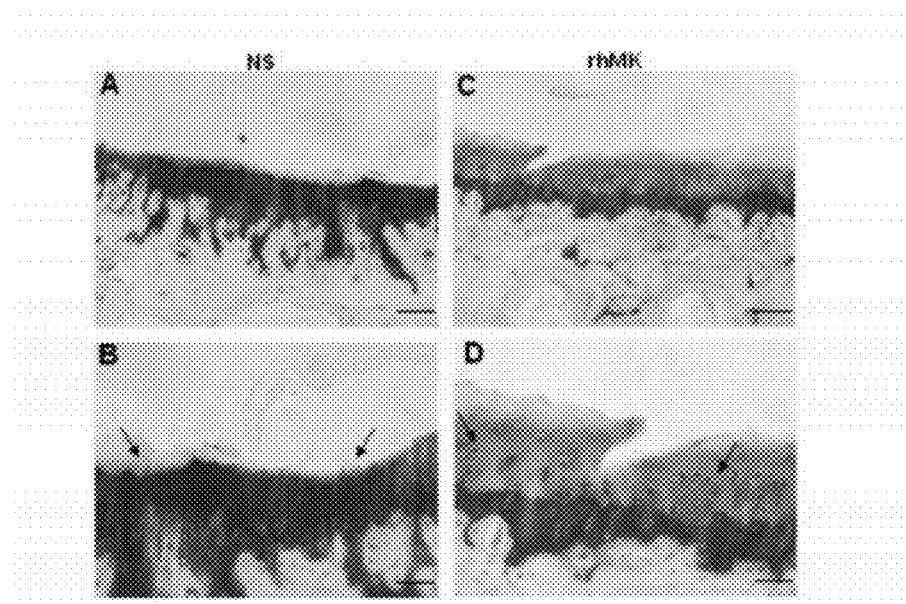
FIG. 3, Histological evaluation of rhMK treated partial damage of rabbit knee articular cartilage. Four weeks after the damage created.

Result. FIG. 3 shows the repair of rabbit knee cartilage partial-thickness injury by rhMK at 4 weeks after the surgery. The left column is the saline treated side (FIGS. 3A and B); the right column is the rhMK treated side (FIGS. 3C and D). The tissue was stained with toluidine blue in FIGS. 3A, B, C, and D. FIGS. 3A and C are low magnification observation, while FIGS. 3B and D are high magnification observation of FIGS. 3A and C respectively. Arrows in FIG. 3B indicate the damage cartilage surface, and arrows in FIG. 3D indicate the injury side filled with regenerated layer of new cartilage.

Figure 4:
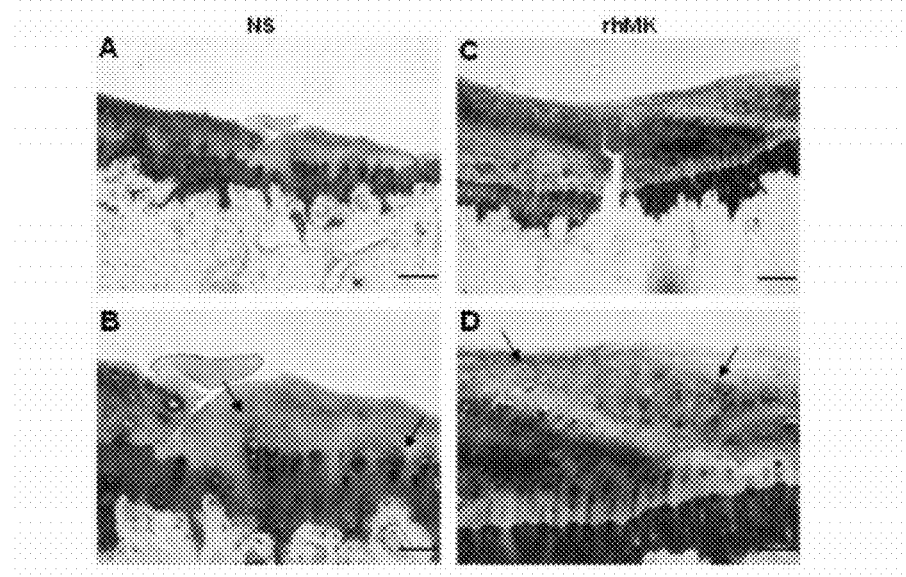
FIG. 4, Histological evaluation of rhMK treated partial damage of rabbit knee articular cartilage. Nine weeks after the damage created.

FIG. 4 shows the repair of rabbit knee cartilage partial-thickness injury by rhMK at 9 weeks after the surgery. The left column is the saline treated side (FIGS. 4A and B), the right column is the rhMK treated side (FIGS. 4C and D). The tissue is stained by toluidine blue in FIGS. 4A, B, C, and D. FIGS. 4A and C are low magnification observation, while FIGS. 4B and D are high magnification observation of FIGS. 4A and C respectively. Arrows in FIG. 4B indicate the damage cartilage surface not covered by new layer of cartilage, and arrows in FIG. 4D indicate the injury side covered by the regenerated layer of new cartilage.

After analyzing the tissue sections of cartilage 4 and 9 weeks after the surgery, we found that rhMK significantly stimulated the growth or regeneration of chondrocytes in the knee cartilage after partial-thickness injury, and repaired the injured cartilage. At 4 weeks after the surgery, there was no new cartilage in the injured area of saline treated side and the proliferation of chondrocytes did not appear (FIGS. 3A and 3B). In sharp contrast, in the rhMK treated side, there were a large number of hypertrophic chondrocytes appeared on the top of the injury site, and the newly formed layer of cartilage was stained lightly with toluidine blue (FIGS. 3C and 3D). A clear separation of regenerated cartilage and the dark-stained residual cartilage was observed (FIGS. 3C and 3D). At 9 weeks after the surgery, the repair-layer of tissue contained few chondrocytes, and stained weakly by toluidine blue (FIGS. 4A and 4B); However, in the rhMK treated side, a thick regenerated layer of cartilage filled with hypertrophic chondrocytes covered the surface of injured cartilage. The regenerated chondrocytes appeared in clusters which resided in new cartilage lacunae and arranged in palisade shapes (FIGS. 4C and 4D). Thus, in the adult rabbit knee cartilage partial-thickness injury model, rhMK repairs the injured cartilage with regenerated cartilage tissues. The new cartilage is originated from the residual chondrocytes, as bone marrow strauma cells in this partial-thickness damage model is not available to fill the damage sites, which is at least a part of the regeneration resource for the repair of full-thickness injury models.

Example 5 rhMK Treats Osteoarthritis Induced by Anterior Cruciate Ligament Transection (ACLT) of Rat Knee Method. 7-week-old male SD rats (250-330 g weight) were anesthetized with 3% pentobarbital sodium (30 mg/kg) by intraperitoneal injection. After anesthesia, the skin was prepared on both sides of the knees. With conventional surgical sterilization and under sterile conditions, the skin and subcutaneous tissue of the knees was cut open from the middle of front knee. The joint capsule was cut along the inner side of the white patellar tendon resulting in patellar dislocation. The anterior cruciate ligament was identified and cut with ophthalmic scissors. The knee was straightened, the patella was relocated, and the wound was sutured layer by layer. Amikacin (100,000 U/ml, injection concentration of 10 mg/kg, a dose of 1 μl/10 g body weight) was injected every day for 4 days to prevent the wound site infection. 14 weeks after the surgery, saline or rhMK was injected into the knee-articular cavity. The rats in sham group without ACLT surgery were not treated; The rats in the ACLT/saline group were injected with 100 μl saline; The rats in ACLT/rhMK-L group were injected with 100 μl rhMK (58.3 μg/kg); In ACLT/rhMK-H group, 100 μl rhMK (525 μg/kg) was given. The injections were given three times one week and continued for two weeks. The rats were maintained in cages with free movement. The rats were sacrificed 2 or 6 weeks after the initiation of the treatments. Their knee-articular cartilage was processed for histological analysis.

Figure 5:
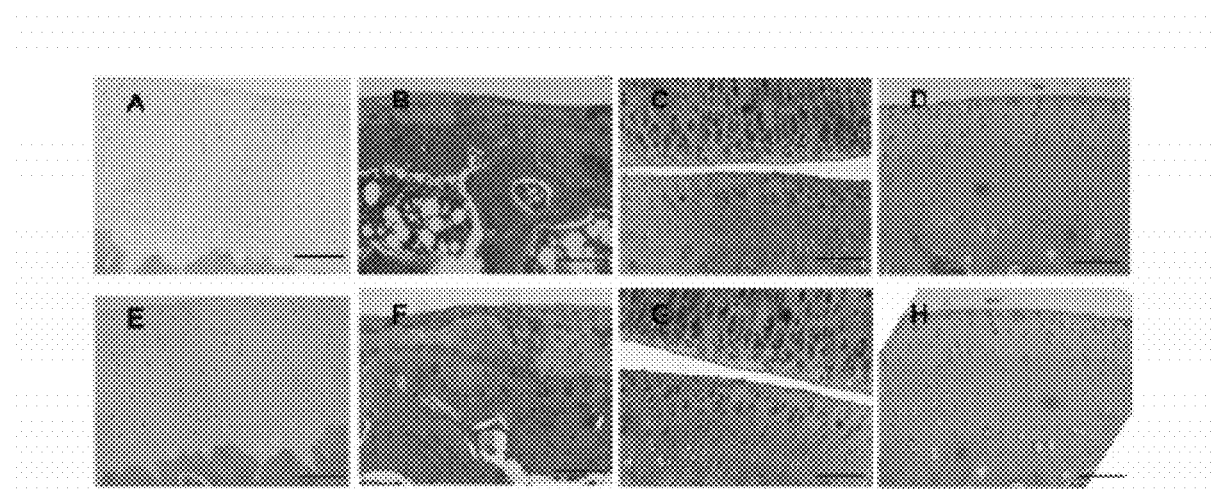
FIG. 5, Histological evaluation of rhMK treated rat knee cartilage damage induced by ACLT (Anterior Cruciate Ligament Transection). Eighteen weeks after the damage created. H&E staining.
Figure 6:
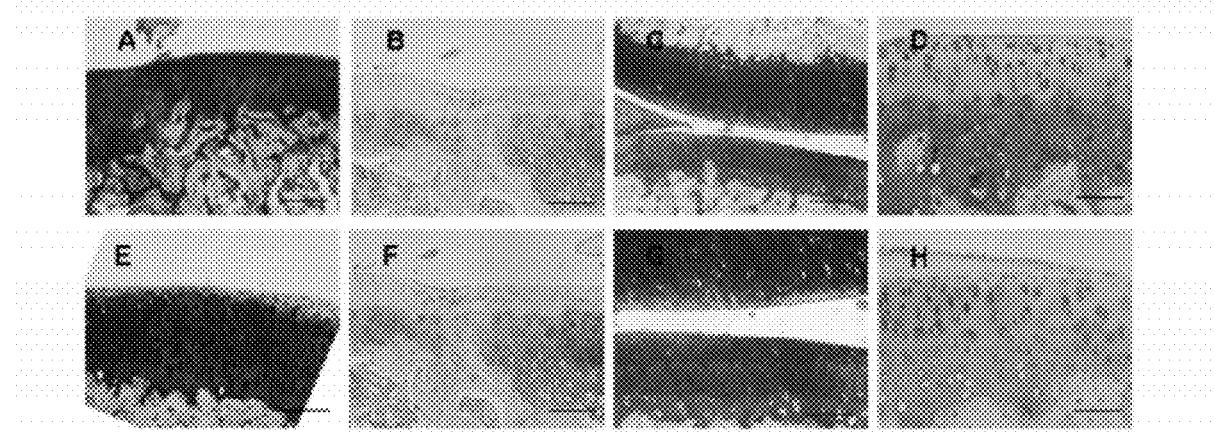
FIG. 6, Histological evaluation of rhMK treated rat knee cartilage damage induced by ACLT (Anterior Cruciate Ligament Transection). Eighteen weeks after the damage created. Toluidine Blue staining for cartilage matrix.

Result. FIGS. 5 and 6 shows the histological structure of the knee articular cartilage at 18 weeks after the ACLT surgery. H&E staining (FIG. 5); Toluidine Blue staining (FIG. 6). (A) The sham Group, (B) the ACLT/saline group, (C) the ACLT/rhMK-L group, (D) the ACLT/rhMK-H group. Bar=200 μm. The E, F, G, H are the high magnifications of A, B, C and D respectively (Bar=100 μm).

In the sham group, normal hyaline cartilage covered the surface of the joint with normal chondrocytes arranged in palisade (FIG. 5A, E). The cartilage was stained positive with Toluidine Blue (FIGS. 6A, E). In the ACLT/rhMK groups, the regenerated cartilage layer was significantly thicker than that of ACLT/saline group. The necrotic chondrocytes are mostly replaced by new chondrocytes which arranged in palisade (FIGS. 5C, G, D, H). The new chondrocytes were hypertrophic chondrocytes resided in cartilage lacunae in clusters, the typical characteristics of chondrocytes. The new layer of cartilage was stained positive with Toluidine Blue a special dye for cartilage matrix proteoglycan (FIG. 6C, G, D, H). In the ACLT/saline group, the surface of the osteoarthritis damaged cartilage was only covered by a few layers of fibrous cells (FIG. 5B, F), and they were stained very weakly by Toluidine Blue (FIG. 6B, F). We conclude that in the ACLT-induced osteoarthritis, rhMK promotes the proliferation of chondrocytes from residual cartilage to form a new layer of cartilage covering the damaged joint cartilage surface. Analysis of the histological scores shows that the ACLT/rhMK groups is statistically lower than that of the ACLT/saline group ($P<0.05$, by Kruskal-wallis Test).

Example 6 rhMK Stimulates the Proliferation of Primary Chondrocytes Isolated from Three Categories of Rat Cartilage Method.

1. Preparation of primary chondrocyte. The 8-week-old male SD rats were sacrificed under sterile conditions. The articular cartilage, fibrocartilage and elastic cartilage tissue were isolated from the femur joints, meniscus and outer ear respectively using a scalpel. The isolated cartilage were cut into small pieces, washed twice with phosphate buffered saline (PBS), and digested with trypsin (0.25% (w/v) trypsin/ 0.02% (w/v) EDTA) at 37° C. for 30 min. The articular cartilage and elastic cartilage were further digested with 0.2% type II collagenase for additional 16 h, and the fibrocartilage were further digested with 0.15% type I collagenase for additional 16 h. After digestion, three chondrocytes were passed through 100 μm filter (Falcon, USA) into 15 ml centrifuge tubes, centrifuged at room temperature at 2000 rpm for 5 min. Cells were resuspended in DMEM containing 10% FBS (fetal bovine serum). Trypan blue staining of the freshly isolated cells was used to monitor the percentage of live cells under the microscope. When the number of live cells is more than 95%, it was used for subsequent experiments.

2. MTT assay. Three types of primary chondrocytes were suspended at a density of $5\times10^4$ cells/ml in DMEM containing 10% FBS. Cells were seeded into a 96-well plate (100 μl per well) and cultured at 37° C. under 5% $CO_2$ for 48 h. The cells were washed with serum-free DMEM medium once. Different concentrations of rhMK (0.5, 1.0, 3.0, 5.0, 9.0 μg/ml) in DMEM (containing 0.5% FBS) were added to each well and the cells were cultured for additional 48 h. After incubation, the medium was replaced with 100 μl serum-free DMEM medium and 20 μl MTT solution (0.5 mg/ml, in PBS), incubated at 37° C. under 5% $CO_2$ for 4 h. After removing the liquid, 120 μl DMSO was added to dissolve the MTT crystals by shaking for 1 min on a micro-plate oscillator. Light absorbance at 490 nm was measured using a microplate reader (BIO-TEK, USA).

3. Culture of primary chondrocytes in monolayer. Three types of primary chondrocytes were suspended in DMEM medium containing 10% FBS, adjusted to $5\times10^4$ cells/ml, added to 6-well plate with 2 ml medium/well, and incubated in 37° C. at 5% $CO_2$. Experiment was divided into two groups: control group and experimental group (with 3 μg/ml rhMK). Cell medium was changed every two days. When the cells grew to the confluence of 85% to 90%, the cells were collected by trypsin digestion, washed in PBS by centrifugation. The cells were resuspended in DMEM containing 10% FBS. Cell survival was monitored by trypan blue staining. Part of the cells were used for cell passage; some were for RNA extraction; some were cytospined onto a glass slide for later immunohistochemical staining and the slides were stored at −80° C. Primary cells or passage 0 (P0) were cultured for 7 days. The newly passaged cells were further cultured in a 6-well plate for 3 days which was then collected by trypsin-digestion and marked as passage P1. The cell amplification at each passage=total number of cells at output/total number of cells at initial input.

4. Serum-free culture. The primary chondrocytes were cultured with DMEM containing 10% FBS for 24 h and washed with serum-free culture medium once. The cells were further cultured with DMEM medium with ITS+1 (composed of insulin-transferrin-selenium, Sigma, USA). Experiment was divided into two groups: control group and experimental group (with 3 μg/ml rhMK). Cell medium was changed every two days. When cells grew to the confluence of 85% to 90%, they were collected by trypsin-digestion and subcultured as previously described.

5. High density culture of chondrocytes. The chondrocytes were harvested and suspended in DMEM containing 10% FBS. The cells were seeded at $4\times10^5$ cells/well into a 24-well plate, and experiment was divided into two groups: control group and experimental group (with 3 μg/m. 1 rhMK). When the cells reached confluence, they were cultured for additional 14 days. The culture medium was changed every two days. After the culture, some of the cells were collected for RNA extraction, and some were treated with trypsin and 0.2% type II collagenase at 37° C. for 30 min. The cells were cytospined onto glass slide and stored at −80° C.

6. Immunohistochemical staining. The cytospined glass slides covered with the cultured chondrocytes under various conditions were stored at −80° C. They were fixed in cold acetone for 10 min, treated sequentially in PBS for 5 min, in 3% $H_2O_2$ (in $ddH_2O$) for 10 min at room temperature, and finally in $ddH_2O$ for 5 min. The slides were covered with 5% BSA (bovine serum albumine) for 20 min at room temperature. The excess serum was removed and the sections were covered with antibody against type II collagen (dilution 1:100) for 30 min at 37° C. The slides were washed three times for 2 min, and incubated with biotin-conjugated goat anti-rabbit IgG (dilution 1:100) for 30 min at 37° C. After washing for three times, the antibody was visualized using DAB. The cells were counterstained with hematoxylin for 30 s, and treated for microscopic observation.

7. RNA extraction and semi-quantitative PCR. Total RNA was extracted from cultured chondrocytes using TRIzol reagent (Invitrogen, China). Isolated RNA (1 μg) was reverse transcribed and then amplified using the reagents from a commercial kit (TAKARA, China) according to the manufacturer's instruction. Table 3 listed the target genes, their GenBank accession numbers, primers, PCR product fragment sizes, annealing temperatures, PCR cycle numbers respectively. Following an initial denaturation step of 2 min at 95° C., amplification consisted of 24-30 cycles of 30 s at 95° C., 30 s at optimal annealing temperature (Tm), and 30 s at 72° C. PCR products were separated on 1.5% (w/v) agarose gels and quantified after staining with ethidium bromide in comparison with internal control gene expression of β-actin.

8. Western blot analysis. Rat primary articular chondrocytes were plated in 24-well plates at cell density of $2 \times 10^5$ cells/cm$^2$ and cultured in DMEM containing 10% FBS, with or without rhMK (3.0 μg/ml). After incubation, cells were lysed in RIPA buffer containing proteinase inhibitors (Beyotime, China). Total protein extracts (15 μg) were resolved by SDS-PAGE, electroblotted on to PVDF membranes, blocked with 5% non-fat milk and probed with 1:1000 dilution of primary antibodies against ERK1/2, phospho-ERK1/2, p38, phospho-p38, JNK, phosphor-JNK, Akt, and phospho-Akt (all from Cell signaling Technology, Beverly, Mass., USA) overnight at 4° C. Antibody-bound protein bands were detected using reagents from the enhanced chemiluminescence kit as described by the manufacturer (Pierce, Holmdel, N.J., USA), and were photographed using Kodak X-OMATLS film (Eastman Kodak, Rochester, N.Y., USA).

9. BrdU incorporation assay of chondrocyte proliferation. Rat primary articular chondrocytes were plated at cell density of $1 \times 10^4$ cells/well in 96-well plates and cultured in DMEM containing 10% FBS, in the absence or presence of various concentrations of rhMK (0.1, 0.3, 1.0, 3.0, 9.0 μg/ml), the inhibitor of MEK1/2, PD98059 (2.8, 8.3, and 25 μM), or the PI3K inhibitor, LY294002 (1.1, 3.3, and 10 μM) for 52 h. Bromodeoxyuridine (BrdU) reagent was added at the final 4 h of culture. BrdU is incorporated into newly synthesized DNA strands of actively proliferating chondrocytes. After partial denaturation of double stranded DNA, BrdU was detected immunochemically (Millipore, Billerica, Mass., USA). Absorbance was measured at 450 nm using an ELX-800 ELISA plate reader (Bio-Tek Instruments, Winooski, Vt., USA) according to the manufacturer's instructions.

Results.

1. rhMK promotes the proliferation of chondrocytes cultured in monolayer. Three types of primary chondrocytes were cultured with or without rhMK in primary monolayer culture without passage. MTT assay was used to determine the proliferative status of the cultured cells. The results are shown in Table 4. rhMK at 3 μg/ml promoted proliferation of all three types of chondrocytes. However, three types of chondrocytes had different sensitivity to rhMK. The lowest effective dose of rhMK for ear elastic cartilage cells is 0.5 μg/ml; for articular chondrocytes, 1 μg/ml; for fibrochondrocyte, 3 μg/ml. Thus, we conclude that rhMK promotes the proliferation of three types of rat primary chondrocyte in monolayer culture in a dose-dependent fashion.

TABLE 3

Target genes for semi-quantitative PCR

| Target Gene | GenBank Accession No. | Forward (5' to 3') Reverse (5' to 3') | Fragment Size (bp) | Tm (C.) | PCR Cycle No. |
|---|---|---|---|---|---|
| Col2a1 | NM_012929 | GAATGGCTGACCTGACCTGATA (SEQ ID NO: 2) | 186 | 54 | 24 |
| | | GGCGTCTGACTCACACCAGATA (SEQ ID NO: 3) | | | |
| Col1a1 | NM_053304 | GGGCAAGACAGTCATCGAATA (SEQ ID NO: 4) | 108 | 50 | 24 |
| | | ATGTCCATTCCGAATTCCT (SEQ ID NO: 5) | | | |
| | | TGGCAGACCAGTACCCGCATCT | | | |
| Sox9 | XM_001081628 | TGGCAGACCAGTACCCGCATCT (SEQ ID NO: 6) | 136 | 54 | 30 |
| | | TCTTTCTTGTGCTGCACGCGC (SEQ ID NO: 7) | | | |
| β-actin | NM_031144 | GAGGCATCCTGACCCTGAAG (SEQ ID NO: 8) | 275 | 54 | 24 |
| | | CATCACAATGCCAGTGGTACG (SEQ ID NO: 9) | | | |

TABLE 4

Dose-response study of rhMK on proliferation of primary chondrocytes cultured in monolayer

| rhMK (µg/ml) | 0 | 0.5 | 1.0 | 3.0 | 5.0 | 9.0 |
|---|---|---|---|---|---|---|
| Articular chondrocyte | 0.27 ± 0.02 | 0.33 ± 0.02 | 0.40 ± 0.01** | 0.38 ± 0.01** | 0.30 ± 0.01** | 0.39 ± 0.01** |
| Auricular chondrocyte | 0.37 ± 0.03 | 0.52 ± 0.05* | 0.54 ± 0.02** | 0.56 ± 0.01** | 0.56 ± 0.02** | 0.56 ± 0.02** |
| Fibrochondrocyte | 0.42 ± 0.02 | 0.42 ± 0.02 | 0.43 ± 0.02 | 0.47 ± 0.00** | 0.45 ± 0.00* | 0.45 ± 0.00* |

The data in the table are values of light absorbance at 490 nm of triplicate cultures in MTT assay, and expressed in mean ± SD. The experiments are repeated three times.
*$P < 0.05$, and **$P < 0.01$, between the indicated group and 0 dose group by Student's t-test.

To further confirm the proliferative role of rhMK to chondrocytes, the proliferation of passaged chondrocytes was analyzed. Three types of rat primary chondrocytes were cultured and passaged for three times referred to P0, P1, and P2. The cellular expansion in each passage was calculated as described in the Method. As shown in Table 5, rhMK promoted the cellular expansion of three types of chondrocytes. Intriguingly, the effect of rhMK on the promotion of fibrochondrocyte growth declined rapidly. Proliferation rate dropped from 112% at P0 passage to 35% in P2 passage. The effect of rhMK on promotion of ear elastic cartilage cell proliferation maintained well (65% in P0 to 55% in P2).

lyzed using semi-quantitative PCR and immunohistochemical staining. The dynamical expression levels of Col2a1, Col1a1 and Sox9 relative to the house-keeping gene β-actin was used to determine the effect of rhMK on the phenotypes of the cells during the passages (P0, P1 and P2) of articular chondrocyte, auricular chondrocyte and fibrochondrocyte.

Figure 7:
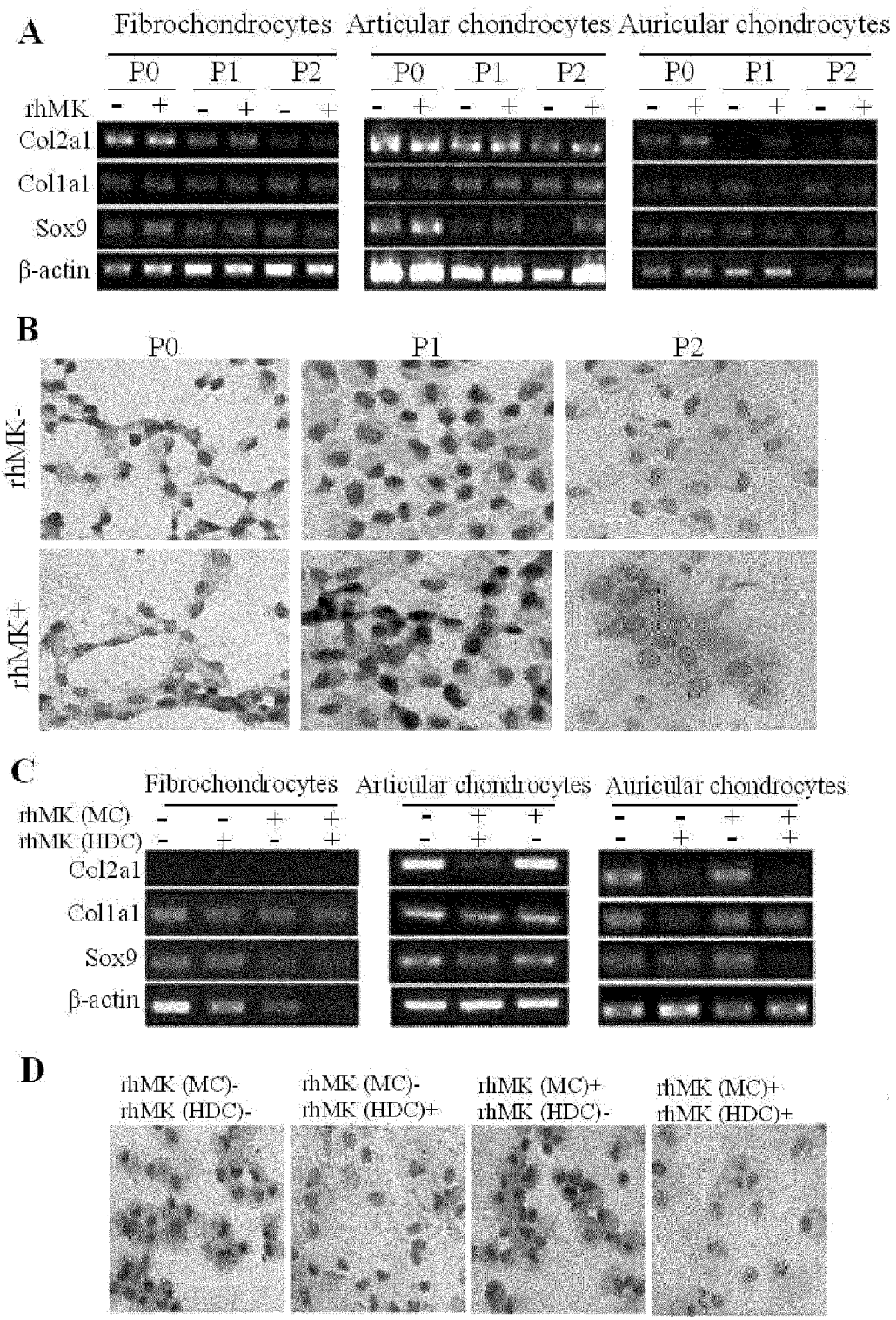
FIG. 7, Functional analysis of rhMK on cultured primary for its roles in chondrocyte dedifferentiation and redifferentiation.

FIG. 7. The effect of rhMK on the dedifferentiation and redifferentiation of rat chondrocyte was shown in FIG. 7. (A) The effect of rhMK on phenotype changes of chondrocytes cultured in monolayer. (B) Immunohistochemical staining of collagen II on auricular chondrocytes cultured in monolayer. (C) The effect of rhMK on chondrocytes cultured in high

TABLE 5 rhMK promotes the growth of rat chondrocyte in monolayer culture

| | P0 | | | P1 | | | P2 | | |
|---|---|---|---|---|---|---|---|---|---|
| | No rhMk Cell expansion (in fold) | rhMK (3 µg/ml) Cell expansion (in fold) | Proliferation rate (%) | No rhMk Cell expansion (in fold) | rhMK (3 µg/ml) Cell expansion (in fold) | Proliferation rate (%) | No rhMk Cell expansion (in fold) | rhMK (3 µg/ml) Cell expansion (in fold) | Proliferation rate (%) |
| Articular chondrocyte | 6.4 ± 0.4 | 13.5 ± 1.2** | 112 | 6.9 ± 0.5 | 12.0 ± 1.4** | 74 | 7.7 ± 0.5 | 11.5 ± 0.5** | 48 |
| Auricular chondrocyte | 4.8 ± 0.3 | 7.9 ± 0.1** | 65 | 9.7 ± 0.7 | 16.1 ± 1.1** | 66 | 5.3 ± 0.6 | 8.2 ± 1.0* | 55 |
| Fibrochondrocyte | 2.5 ± 0.7 | 5.3 ± 1.3* | 110 | 18.6 ± 1.8 | 28.1 ± 3.4* | 51 | 15.5 ± 2.0 | 20.9 ± 0.9* | 35 |

Tables shown represent mean ± SD from triplicate cultures. Data are expressed as cell expansion in fold for primary culture (P0), passage 1 (P1) and 2 (P2). Proliferation rate (%) = Cell expansion with rhMK/Cell expansion without rhMK. The experiments are repeated three times.
*$P < 0.05$, and **$P < 0.01$, compare the data from the cultures with or without rhMK by Student's t test.

Interestingly, when three types of chondrocytes were cultured in serum-free medium, they formed cell clusters without attachment to the culture flask bottom. Addition of rhMK (3 µg/ml) did not make the cell attachment and proliferation. However, when the chondrocytes were cultured first in DMEM supplemented with 10% FBS for 24 h, the cells could be cultured further with serum-free medium. Addition of rhMK (3 mg/ml) to the serum-free medium promoted the cell expansion by 34%, 51%, and 18% for passage 1, 2, and 3 respectively over the control cultures without rhMK.

In summary, the data demonstrate that rhMK stimulates the proliferation of three types of chondrocytes. The role of rhMK is affected by the culture conditions and the cell status in cultures. The primary chondrocytes after several passages eventually lost their response to rhMK, which may be caused by the loss of chondrocyte characters during culture passages.

2. The effects of rhMK on phenotype of chondrocyte cultured in monolayer. The primary chondrocytes cultured in monolayer differentiates spontaneously into fibroblast-like cells. After determination on the proliferation effect of rhMK on the three types of chondrocytes, the role of rhMK on the cellular phenotypes of the cultured chondrocytes were anadensity. (D) Immunohistochemical staining of collagen II on auricular chondrocytes cultured in high density. MC, monolayer culture; HDC, high density culture.

The results indicate that rhMK has no significant effect on the phenotype of fibrochondrocyte and articular chondrocyte (FIG. 7A). After three passages of fibrochondrocyte, the gene expression levels of Col2a1 decreased three folds with or without rhMK Immunohistochemical staining and semiquantitative PCR of collagen II had similar results on fibrochondrocyte and articular chondrocyte during three passages with or without rhMK. Therefore, rhMK has no significant effect on the phenotypes of fibrochondrocytes and articualr chondrocytes during culture passages. rhMK can not inhibit the dedifferentiation, the loss of chondrocyte phenotype, of two types of chondrocytes during the monolayer culture. Interestingly, after one passage of auricular chondrocyte, the expression of Col2a1 was significant decreased and was not detected by semiquantitative PCR, but when the rhMK was added into the medium, rhMK inhibited the decreasing of the Col2a1 (FIG. 7A). Collagen II was not detected in passage one chondrocytes without rhMK through immunohistochemical staining. But there were about 50% chondrocytes stained collagen II positive in the rhMK group (FIG. 7B). The results show that rhMK inhibits dedifferentiation of auricular chondrocytes cultured in monolayer.

3. rhMK inhibits redifferentiation of high-density cultured chondrocytes. It is well known that high-density culture promotes the dedifferentiated chondrocyte redifferentiates into chondrocytes. To analyze the redifferentiation potential of the rhMK treated chondrocytes, the chondrocytes initially cultured with or without rhMK were subjected to high-density culture with or without rhMK (FIG. 7C, D). Articular chondrocytes at passage 6 (P6), fibrochondrocyte and auricular chondrocytes at passage 3 (P3) were confirmed negative in expression of Col2a1 by PCR and immunohistochemical staining cultured with or without rhMK in monolayer. The dedifferentiated cells were cultured in high-density with or without rhMK, and analyzed for their phenotypes. The results show that rhMK had no effect on the Col2a1 re-expression in the P3 fibrochondrocytes that had no Col2a1 expression and were cultured in high-density (FIG. 7C), and the immnohistochemical staining of Collagen II was also negative (data not shown). While the P6 articular chondrocyte and P3 auricular chondrocyte cultured in monolayer with or without rhMK re-expressed Col2a1 after high-density culture, the Col2a1 expression level was significantly inhibited in high-density cultures with rhMK (FIGS. 7C and 7D). Thus, the results demonstrate that rhMK does not affect the differentiation potential of the primary chondrocytes culture in monolayer, and it inhibits redifferentiation of the dedifferentiated chondrocytes in high-density cultures.

This invention completely differs from present technology of MK. The experimental results demonstrate that MK promotes the proliferation of three types of chondrocyte and cures cartilage disease as new drugs which will provide new choice for clinical therapy of cartilages diseases. Meanwhile, MK can also be used for cell expansion in vitro for cartilage tissue engineering.

The scope of this invention is not restricted by the particular embodiments described in this application, which are intended as single illustrations of individual aspects of the invention. The scope of this invention also includes the methods and components with the same function of MK. Many modifications and variations of this invention can be made without departing from its spirit and scope, as will be apparent to those skilled in the art. Such modifications and variations are intended to fall within the scope of the appended claims. The full texts of the literatures cited are included in this application for reference.

What is claimed is:

1. A method for treating a degenerative cartilage disease in a subject in need thereof, the method comprising administering to the subject at a site in need of treatment an effective amount of a protein consisting of the amino acid sequence of SEQ ID NO: 1, wherein the degenerative cartilage disease is selected from the group consisting of osteoarthritis and intervertebral disc degeneration, wherein the effective amount is 10 µg/kg/day to 300 µg/kg/day.

2. The method of claim 1, wherein the administering comprises implanting into the subject a medical device which comprises an effective amount of the protein.

3. The method of claim 2, wherein the medical device is in the form of a scaffold which comprises an effective amount of the protein.

4. The method of claim 3, wherein the scaffold comprises collagen IIa.

5. The method of claim 1, wherein the effective amount is 300 µg/kg/day.

6. A method for treating traumatic cartilage damage in a subject in need thereof, the method comprising administering to the subject at a site in need of treatment an effective amount of a protein consisting of the amino acid sequence of SEQ ID NO: 1, wherein the effective amount is 10 µg/kg/day to 300 µ/kg/day.

7. The method of claim 6, wherein the effective amount is 300 µg/kg/day.

* * * * *